United States Patent [19]

Weuste et al.

[11] Patent Number: 5,430,187
[45] Date of Patent: Jul. 4, 1995

[54] METHOD FOR MANUFACTURING DIBENZYLAMINE

[75] Inventors: Burkhard Weuste, Gummersbach; Manfred Bergfeld, Erlenbach, both of Germany

[73] Assignee: Akzo N.V., Arnhem, Netherlands

[21] Appl. No.: 244,223

[22] PCT Filed: Dec. 16, 1992

[86] PCT No.: PCT/EP92/02918

§ 371 Date: May 17, 1994

§ 102(e) Date: May 17, 1994

[87] PCT Pub. No.: WO93/13047

PCT Pub. Date: Jul. 8, 1993

[30] Foreign Application Priority Data

Dec. 21, 1991 [DE] Germany ............ 41 42 694.0

[51] Int. Cl.⁶ .................................... C07C 209/24
[52] U.S. Cl. ........................................... 564/391
[58] Field of Search ................................ 564/391

[56] References Cited

U.S. PATENT DOCUMENTS 2,217,630 10/1940 Winans ........................ 549/472
3,293,891 12/1975 Greenfield et al. ............ 564/385

FOREIGN PATENT DOCUMENTS 2118283 11/1972 Germany.

OTHER PUBLICATIONS

*Synthesis* (1). 70–74 (Jan. 1979).
*J. Organomet. Chem.* 208(2) 249–251 (1981).
*Chemistry Letters* (6), 889–890 (1984).
*Indian J. Technol.* 23(7), 266–268 (Jul. 1985).
*Ullmanns Encyclopadie der technischen Chemie*, 4th Edition, vol. 8, 440–441 (1974).
*Introduction to Organic Chemistry*, 4th Edition, A. Streitwieser and C. H. Heathcook, 1990, pp. 782–784 (corresponding to German text, attached, pp. 927–928).
*J. American Chem. Soc* 61, 3566–67 (Jul.–Dec. 1939).

*Primary Examiner*—Richard L. Raymond
*Attorney, Agent, or Firm*—Oliff & Berridge

[57] ABSTRACT

The method for manufacturing dibenzylamine by reacting benzaldehyde and ammonia in the presence of hydrogen and a hydrogenation catalyst in an inert organic solvent is characterized by the fact that the reaction is conducted with an ammonia ratio of >0.5 mol per mol benzaldehyde and with a hydrogenation catalyst containing a platinum metal and/or a ferrous metal on a carrier. The method is performed at low temperatures, preferably 40°–90° C. In particular, a high selectivity for dibenzylamine of more than 90% is achieved with practically complete benzaldehyde conversion.

12 Claims, No Drawings

METHOD FOR MANUFACTURING DIBENZYLAMINE

FIELD OF THE INVENTION

This application is a 371 of PCT/EP92/02918 filed Dec. 16, 1992.

The present invention relates to a method of manufacturing dibenzylamine from benzaldehyde and ammonia with catalytic hydrogenation.

BACKGROUND

Dibenzylamine does not form any carcinogenic nitrosamines and can be used as a starting compound for manufacturing the vulcanization accelerator tetrabenzylthiuram disulfide, which also forms only nitrosamines of low volatility that remain in the rubber. The manufacture and use of this vulcanization accelerator is therefore largely harmless to health.

Dibenzylamine is specifically manufactured by hydrogenation of benzonitrile with Pt catalysts (U.S. Pat. No. 3,923,891). Other suggested syntheses for dibenzylamine start with benzylamine (Synthesis (1), 70 (1979); J. Organomet. Chem. 208 (2), 249 (1981); Chem. Lett. (6), 889 (1984); Ind. J. Technol. 23 (7), 266 (1985)). In addition, dibenzylamine occurs as a byproduct in the industrial synthesis of benzylamine from benzaldehyde by reaction with ammonia and catalytic hydrogenation with Raney nickel (Ullmanns Encyclopädie der technischen Chemie, 4th edition, Volume 8, 440):

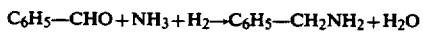

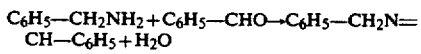

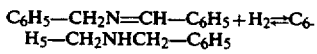

Dibenzylamine is therefore formed via the stages of monobenzylamine and N-benzylbenzylidenimine and can be separated from the intermediate reaction mixture by fractionation. The reaction mixture can also contain tribenzylamine as a secondary product, and benzyl alcohol and toluene as reduction products of benzaldehyde. According to Ullmanns Encyclopädie, Volume 8, Page 440, in the reaction a mixture of 470 kg monobenzylamine, 2 kg benzylbenzylidenimine, 1 kg dibenzylamine, and 1 kg benzyl alcohol is obtained, for example, from 500 kg of benzaldehyde (4.72 mol) and 110 kg ammonia (6.47 mol)—in other words, with a stoichiometric excess of ammonia at 100° C.

In addition, J. Amer. Chem. Soc. 61 (1939), Page 3566 describes the manufacture of monobenzylamine with dibenzylamine as a byproduct, by reacting benzaldehyde with a mere stoichiometric excess of ammonia under conditions of catalytic hydrogenation with Raney nickel as the catalysts. According to the example cited therein, a mixture of 287 g monobenzylamine and 21.7 g dibenzylamine is obtained from 3 mol benzaldehyde and 3 mol ammonia—in other words, using stoichiometric amounts relative to monobenzylamine formation, but using a stoichiometric excess of ammonia relative to dibenzylamine formation, at 70° C. On the other hand, according to Table 1 of this citation, the amount of dibenzylamine can predominate (80.8% versus 11.8% monobenzylamine) when using stoichiometric amounts of benzaldehyde and ammonia (½ equivalent) relative to dibenzylamine formation.

SUMMARY OF THE INVENTION

Hence, there is a need for an economic method of manufacturing dibenzylamine from benzaldehyde and ammonia by catalytic hydrogenation. The goal of the present invention is to provide such a method in which, in particular, a higher selectivity for dibenzylamine is achieved and a catalyst that is easier to handle can be used, and yet smaller amounts of catalyst metal are required.

This goal is achieved by the invention, which comprises a method of manufacturing dibenzylamine by reacting an amount of benzaldehyde and an amount of ammonia in the presence of hydrogen and a hydrogenation catalyst in an inert organic solvent, wherein the reaction is performed with an ammonia concentration of >0.5 mol ammonia per mol benzaldehyde and with a hydrogenation catalyst comprising at least one platinum metal, and/or a ferrous metal on a carrier.

The advantageous result according to the invention—especially the high selectivity for dibenzylamine, over 90%, with practically complete benzaldehyde conversion—is very surprising given the prior art cited at the outset. With regard to the molar ratio of reactants benzaldehyde and ammonia, the prior art discourages the excess ammonia to be used according to this invention (>0.5, 0.8, or 1.0 mol ammonia per mol of benzaldehyde correspond to a stoichiometric excess of >0%, 60%, or 100% respectively, relative to dibenzylamine formation). The ammonia excess used according to this prior art relative to dibenzylamine formation (according to Ullmanns Encyclopädie, Volume 8, Page 440, or J. Amer. Chem. Soc. 62, Page 3567, 1.37 mol or 1 mol ammonia per mol benzaldehyde) produces monobenzylamine as the main product and not dibenzylamine. In addition, the experimental results in J. Amer. Chem. Soc. 61, Page 3567 even suggest a deficiency of ammonia to increase the dibenzylamine yield. Excess ammonia was therefore not only not suggested by the prior art, but was even advised against.

A more remote example of prior art according to German patent document DE-A-21 18 283—relating to the manufacture of secondary or tertiary aliphatic amines by reacting aliphatic carbonyl compounds and an amine or ammonia under catalytic hydrogenation conditions—does describe excess ammonia. However, since this document specifies process conditions and also starting compounds which differ considerably from the present invention, the latter was in no way suggested by the content of DE-A 21 18 283.

Thus, the reaction according to DE-A-21 18 283 takes place at very high temperatures of at least 130° C., specifically, 180° C. to 200° C. in the case of their single Example 15 relating to the use of ammonia (in contrast, the present invention is practiced preferably below 100° C.). The prior art is practiced in the absence of a solvent with very large excesses of ammonia (up to 8 mol amine per mol of carbonyl compound and in their Example 15, 4 mol ammonia per mol of cyclohexanone), and in the presence of a special catalyst ("a mixture of silver and palladium known as a catalyst by itself, applied to a carrier sintered by heating"). The method of DE-A-21 18 283 uses no special aromatic carbonyl compound such as benzaldehyde, but rather a (cyclo)aliphatic carbonyl compound (in Example 15, cyclohexanone) is used, which cannot be readily compared in terms of its reactivity. Under these conditions, only a relatively low yield of secondary amine was achieved by DE-A-21 18 282 (according to their Example 15, 73% dicyclohexylamine and 18% monocyclohexylamine, 1-2% corresponding imine, and 2% cyclohexanol).

Accordingly, there was a considerable prejudice in the field against the use of ammonia in excess or in equal molecular amounts because of the related prior art described at the outset. This is also confirmed by the recent textbook "Organische Chemie" [Organic Chemistry] by A. Streitwieser and C. H. Heathcook, Verlag Chemie, 1990, Pages 927 and 928, where it states that the reaction of monobenzylamine to form dibenzylamine can be suppressed by excess ammonia—in other words, dibenzylamine is not promoted but even suppressed.

The excess ammonia is therefore important to the invention. With increasing excess in ammonia, the selectivity for dibenzylamine increases further, accompanied by a surprisingly strong suppression of direct hydrogenation of benzaldehyde to benzyl alcohol (which is known normally to occur very readily), and by a suppression of tribenzylamine formation with a slight increase in monobenzylamine formation, especially when non-sulfided catalysts are used. In contrast, sulfided catalysts advantageously suppress the formation of benzyl alcohol and toluene much more strongly, but this is associated with an increase in the amount of tribenzylamine. When sulfided catalysts are used, an increase in the amount of ammonia essentially leads only to a shift in the ratio of tribenzylamine to monobenzylamine, in favor of the latter. Finally, when relatively high amounts of ammonia are used, a decrease in selectivity for dibenzylamine is observed once again.

DETAILED DESCRIPTION OF THE INVENTION

The method according to the invention is therefore preferably conducted with an ammonia concentration in the range of 0.8 to 4 mol ammonia, and especially preferably from 1 to 3 mol ammonia, per mol benzaldehyde.

The method according to the invention is advantageously conducted at low temperatures, up to 100° C. maximum, preferably in the range from 40° C. to 90° C. and especially preferably from 60° C. to 90° C. At higher temperatures, the dibenzylamine selectivity decreases, apparently as the consequence of transalkylation. The formation of benzyl alcohol increases sharply at lower temperatures.

The elements in positions 44 to 46 and 76 to 78 of the periodic table—preferably ruthenium, palladium, and platinum—are understood to be the platinum metals included in the hydrogenation catalyst of the invention; and the elements with Nos. 26 to 28—preferably cobalt and nickel—are understood to be the ferrous metals. The platinum metals can be used especially advantageously in their sulfided form.

The amount of catalyst required for the method according to the invention is surprisingly small: a maximum of 0.5 wt. % and preferably a maximum of 0.2 wt. % platinum metal or ferrous metal, relative to the amount of benzaldehyde used, is required.

According to the invention, known coarse-surfaced materials are used as carriers for the hydrogenation catalyst, such as: activated charcoal; aluminum oxide and materials containing aluminum oxide; silicic acid, silicates, and materials containing silicates, such as silica gel; diatomaceous earth; kaolin; talc; and clays, preferably from the group consisting of activated charcoal, aluminum oxide, silica gel, and diatomaceous earth.

Preferably, the method of the invention is conducted with a hydrogenation catalyst containing palladium on a carbon carrier.

By adding co-catalysts (for example, catalytic quantities of methanesulfonic acid) the dibenzylamine selectivity of the method according to the invention can be increased even further.

According to the invention, liquids such as those conventionally used in the catalytic hydrogenation of carbonyl compounds are primarily used as inert organic solvents, in which the ammonia can be dissolved to form a homogeneous liquid phase of the reaction mixture. Such liquids can be: water; water-miscible alcohols, preferably methanol; as well as water-miscible ethers, such as dioxane, tetrahydrofuran, ethylene glycol dimethyl ether, or ethylene glycol diethyl ether.

The execution of the method according to the invention is very simple. For example, a simple metal autoclave can be used which is equipped with a gassing turbine, bottom drain, heater, and stirrer. The autoclave is loaded with the benzaldehyde, very small quantities of catalyst on a carrier, and a solution containing ammonia, then charged with hydrogen until no more hydrogen is taken up at reaction temperature. The reaction times are advantageously only 10 to 45 minutes. After the reaction mixture is drained and the catalyst filtered off, it can then be simply separated by drawing off the solvent, followed by fractional distillation (cf. Ullmanns Encyclopädie der technischen Chemie, 4th edition, Volume 8, Page 440). In general, depending on the desired application of the dibenzylamine, it can suffice to distill off the solvent and most of the low-boiling components of the reaction mixture, whereupon no additional purification steps are required.

A special advantage lies in the separability and regenerability of the catalyst used on the carrier according to the present invention, in contrast to the prior art using Raney nickel.

The method of the invention thus offers an economical method of making dibenzylamine with high selectivity. It can also be implemented in a continuous process.

The present invention will be described in greater detail in the following examples.

EXAMPLES 1 TO 4

A 500-ml Büchi steel autoclave filled with inert gas and fitted with a hollow shaft gassing turbine was charged with 21.2 g (0.2 mol) benzaldehyde and the following amounts of ammonia in methanol: 2.72 g (Example 1), 6.8 g (Example 2), 10.2 g (Example 3), and 13.6 g (Example 4) of ammonia. Then 0.85 g palladium catalyst—Type E101 R/W from Degussa (5% Pd on carbon; approximately 50% $H_2O$)—was added and rinsed with sufficient methanol that the reaction mixture contained about 10% benzaldehyde. The reaction mixture was pressurized twice with hydrogen and heated under $5 \cdot 10^5$ Pa hydrogen pressure to 70° C. Then it was pressurized at $20 \cdot 10^5$ Pa until no further hydrogen was taken up. After cooling and decompression, the solution was drained through a frit to separate the solid catalyst and used directly for gas chromatographic analysis. Finally, the solvent was evaporated off by a rotary vacuum evaporator and the resultant oily product was weighed (approximately 20 g).

The composition of this crude product, as in the other examples, was determined by gas chromatography.

The following compositions were found (in addition to small amounts of other byproducts):

| Experiment No. | mol NH₃ per mol BA | MBA | DBA | TBA | BOH (% area) |
|---|---|---|---|---|---|
| 1 | 0.8 | 0.2 | 84.5 | 1.8 | 9.1 |
| 2 | 2.0 | 2.2 | 85.2 | 0.3 | 8.0 |
| 3 | 3.0 | 4.4 | 90.3 | — | 1.2 |
| 4 | 4.0 | 7.8 | 87.8 | — | 0.8 |

BA = benzaldehyde
MBA = monobenzylamine
DBA = dibenzylamine
TBA = tribenzylamine
BOH = benzyl alcohol

EXAMPLES 5 TO 7

The same procedure was used as in Example 1, but instead of the catalyst used in that example, a sulfided palladium catalyst, was used: Type E101 RS/W from Degussa (5% Pd on carbon) for Examples 5 and 7, or Type Escat (reduced) from Engelhardt (5% Pd on carbon) for Example 6 was used. In addition, the amount of ammonia in Example 6 was 3.4 g (1.0 mol NH₃ per mol BA) and in Example 7, 5.1 g (1.5 mol NH₃ per mol BA).

This resulted in products with the following compositions (% area): 0.1 monobenzylamine—83.9 dibenzylamine—10.2 tribenzylamine—2.9 benzyl alcohol (Example 5), 1.7 monobenzylamine—84.3 dibenzylamine—7.1 tribenzylamine—1.6 benzyl alcohol (Example 6) and 2.8 monobenzylamine—93.3 dibenzylamine—1.0 tribenzylamine—1.0 benzyl alcohol (Example 7).

EXAMPLES 8 AND 9

The same procedure was used as in Example 7, not at a reaction temperature of 70° C. but rather at 50° C. (Example 8) and at 90° C. (Example 9). The resulting products had the following compositions (% area): 70.0 DBA—0.2 TBA—29.5 BOH (Example 8); and 11.6 MBA—84.7 DBA—1.7 TBA (Example 9).

EXAMPLES 10 TO 12

The same procedure was used as in Example 1 but with 5.1 g ammonia and, instead of the catalyst used in Example 1, a platinum catalyst (non-sulfided), Type F101B from Degussa (5% Pt on carbon) (Example 10), a sulfided platinum catalyst, Type F101RSH from Degussa (5% Pt on carbon) (Example 11), and a ruthenium catalyst (non-sulfided), Type H 101 BW from Degussa (5% Ru on carbon) (Example 12). This resulted in products with the following composition (% area): 2.6 MBA—80.1 DBA—0.6 TBA—6.1 BOH (Example 10), 6.6 MBA—76.5 DBA—0.6 TBA—1.9 BOH (Example 11), and 82.0 DBA—1.7 TBA—1.5 BOH (Example 12).

EXAMPLE 13

This example describes the use of a catalyst without a carrier.

The procedure was the same as in Example 1, but used 6.8 g ammonia and, instead of the catalyst used in Example 1, 1 g of Raney nickel from Merck, catalog No. 820875 (50% water) was used. This resulted in a product with the following composition (% area): 1.3 MBA—5.6 DBA—89.2 BOH. Hence, only benzyl alcohol was formed for the most part.

We claim:

1. A method for manufacturing dibenzylamine, comprising reacting in an inert organic solvent an amount of benzaldehyde and an amount of ammonia in the presence of hydrogen and of a hydrogenation catalyst on a carrier, wherein the reaction is conducted with an ammonia concentration of greater than 0.5 mol ammonia per mol benzaldehyde and the hydrogenation catalyst comprises at least one member of a group consisting of platinum metals and ferrous metals.

2. The method according to claim 1, wherein the ammonia concentration is 0.8 to 4 mol ammonia per mol benzaldehyde.

3. The method according to claim 1, wherein the ammonia concentration is 1 to 3 mol ammonia per mol benzaldehyde.

4. The method according to claim 1, wherein the reaction is conducted at a temperature of up to 100° C.

5. The method according to claim 1, wherein the reaction is conducted at a temperature of 40° C. to 90° C.

6. The method according to claim 1, wherein the reaction is conducted at a temperature of 60° C. to 90° C.

7. The method according to claim 1, wherein the hydrogenation catalyst comprises a sulfided platinum metal.

8. The method according to claim 1, wherein the hydrogenation catalyst is used in an amount of up to 0.5 wt. %, relative to the amount of benzaldehyde used.

9. The method according to claim 1, wherein the hydrogenation catalyst is used in an amount of up to 0.2 wt. %, relative to the amount of benzaldehyde used.

10. The method according to claim 1, wherein the carrier for the hydrogenation catalyst comprises at least one member selected from the group consisting of activated charcoal, aluminum oxide, silica gel, and diatomaceous earth.

11. The method according to claim 7, wherein the carrier for the hydrogenation catalyst comprises at least one member selected from the group consisting of activated charcoal, aluminum oxide, silica gel, and diatomaceous earth.

12. The method according to claim 1, wherein the hydrogenation catalyst comprises palladium and the carrier comprises carbon.

* * * * *